United States Patent [19]

Reichl et al.

[11] 4,294,407

[45] Oct. 13, 1981

[54] ATOMIZER FOR FLUIDS, PREFERABLY AN INHALATION DEVICE

[75] Inventors: Ernst Reichl, Munich; Herbert Marloth, Siegertsbrunn, both of Fed. Rep. of Germany

[73] Assignee: Bosch-Siemens Hausgeräte GmbH, Stuttgart, Fed. Rep. of Germany

[21] Appl. No.: 104,581

[22] Filed: Dec. 17, 1979

[30] Foreign Application Priority Data

Dec. 19, 1978 [DE] Fed. Rep. of Germany ....... 2854841

[51] Int. Cl.³ ............................................ A61M 11/00
[52] U.S. Cl. ............................. 239/102; 128/200.16; 239/338; 261/DIG. 65
[58] Field of Search ...................... 128/200.16, 200.23; 261/DIG. 48, DIG. 65; 239/4, 102, 338

[56] References Cited

U.S. PATENT DOCUMENTS 3,738,574 6/1973 Guntersdorfer et al. .......... 239/102
4,119,096 10/1978 Drews .............................. 239/102 X

FOREIGN PATENT DOCUMENTS 2107310 8/1971 Fed. Rep. of Germany ...... 239/102
1434746 5/1976 United Kingdom ................ 239/102

Primary Examiner—Andres Kashnikow
Attorney, Agent, or Firm—Herbert L. Lerner; Laurence A. Greenberg

[57] ABSTRACT

Atomizer for fluid, including an atomizer housing, a unitary fluid container removably inserted in the housing, an atomizing element activatable by ultrasonic flexural vibrations being disposed in the housing, means integral with the fluid container for transporting the fluid from the fluid container to the atomizing element, and manually activatable means for operating the transporting means and atomizing element.

9 Claims, 4 Drawing Figures

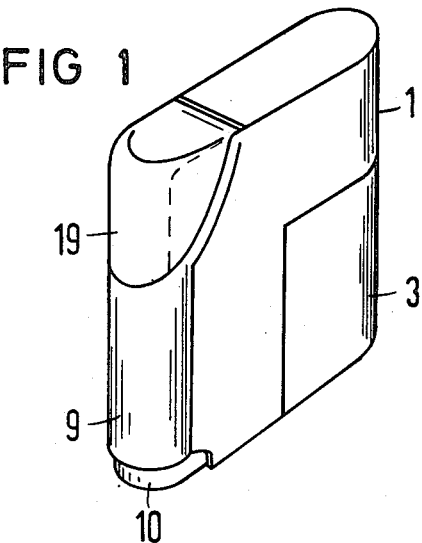
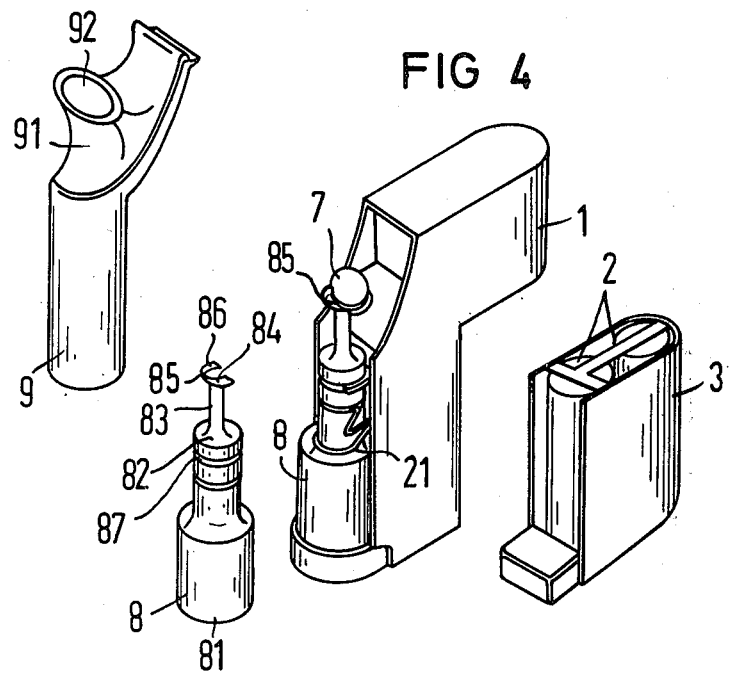

ATOMIZER FOR FLUIDS, PREFERABLY AN INHALATION DEVICE

The invention relates to an atomizer for fluids, preferably an inhalation device having an atomizing element activated by ultrasonicflexural vibrations, and being connectible with the contents of an exchangeable fluid container which supplies fluid during operation.

The known atomizers for fluids of the above-mentioned type have a storage space in the housing of the device in which a fluid container with a small discharge opening can be inserted and secured. Such atomizers for fluids are used as inhalators, as hairspray or roomspray sprayers or the like. As a rule, the spraying agents contain volatile components such as alcohol, for example. For economic reasons, the fluid containers should be large enough, so that they can contain liquid to be atomized for several inhalations or general spraying applications. Because of this, difficulty arises after storing the fluid container for a longer time period, in that the volatile components of the fluid escape through the open discharge opening, or that, if there are any means to transport the fluid, such as a wick, for example, in the discharge opening, there exists the danger that the discharge opening will clog, and further discharge will become restricted or impossible.

In the known inhalation devices, which are filled, for example, with a medically active fluid, and which serve for the treatment of the breathing passages, for example in asthma patients, the metering or dosing of the active liquid agent is effected in a mechanical way, by means of a trigger mechanism by which the spray valve can be operated for short time periods. For the transport of the fluid, chemical gases are used as propellants. Recent investigations of such propellant gases have raised fears that these gases have detrimental side effects with respect to human health, so that the trend is to find ways to atomize fluids without using such propellant gases. For the application of inhalation devices for medical purposes it is particularly important, besides the accurate metering of the fluid, that the used fluid in the fluid container is to a great extent closed off from the outer atmosphere.

It is accordingly an object of the invention to provide an atomizer for fluids, preferably an inhalation device which overcomes the hereinafore mentioned disadvantages of the heretofore known devices of this general type, in such a manner that the required liquid is withdrawn as needed from a container which is closed when not in operation, and is finely atomized without the aid of a gas as a propellant, whereby particular consideration is given to achieving a simple, problem free construction of the device, and to provide convenient handling and mounting for the fluid container.

With the foregoing and other objects in view there is provided, in accordance with the invention, an atomizer for fluid, preferably an inhalator, comprizing an atomizer housing, unitary fluid container removably inserted in the housing, an atomizing element activatable by ultrasonic flexural vibrations being disposed in the housing, means integral with the fluid container for transporting the fluid from the fluid container to the atomizing element, and manually activatable means for operating the transporting means and atomizing element. Thereby one can use, in principle, a conventional cartridge type pocket-fluid dispenser, which comprises two parts that can be moved with respect to each other by manual pressure, and which contains a discharge valve, and a displacement-discharge mechanism, that works in conjunction with the latter and which is operated by pressing the above mentioned parts together. To avoid entry of air into the fluid supply after the displacement action in all circumstances, according to a further development of the invention, provisions are made for providing the fluid dispenser with a discharge valve and with displacement-discharge means working together with the discharge valve, and for filling it with gas which creates a positive pressure, thereby using a gas which is harmless for the human organism.

In accordance with another feature of the invention, the fluid container is air tight and includes means for preparing or readying a metered portion of fluid, preferably a medically active substance, for transport, and the transporting means is operable to transport the metered portion of fluid.

In accordance with a further feature of the invention there are provided a discharge orifice formed in the housing, and a preparatory element in vicinity of the orifice and atomizing element for retaining the metered portion of transported fluid.

In accordance with an added feature of the invention, the preparatory element is a pan having an opening formed therein facing the atomizing element, and there is provided a fluid rebound shield integral with the pan and extending over the orifice.

In accordance with an additional feature of the invention, the fluid container includes a discharge valve, a gas under positive pressure, and displacement-transport means operable with the valve.

By making the fluid dispenser and the means for supplying the fluid as an integral unit which is completely closed when not in operation, and by virtue of the fact that with the operation of a single operating member a transport of the fluid and the metering of the fluid can be effected, and also the activation of the atomizing element and of its vibration generator is achieved, several important results are realized. These are, on the one hand, a very simple and uncomplicated construction of the atomizer itself, because there is no longer any need for special transport or supply elements in the body of the device, and, on the other hand, the assurance that the fluid will not come in contact with the outer atmosphere when the device is not in use. It therefore becomes possible, even for medical treatments, to dimension the fluid dispenser so that it contains enough fluid for many dosages which, if necessary, can remain in the atomizer for a long period of time.

In accordance with yet another feature of the invention, the fluid container has two parts which are compressible for activating the transporting means and discharge valve and the operating means includes a member disposed in the housing, and including a housing support for fixing one of the parts in position relative to the atomizing element, and a spring exerting a force on the member in a given direction, the fluid container being insertable in the slideable member and the member being manually displaceable in the housing against the given direction for compressing the parts.

In accordance with yet a further feature of the invention, there are provided a vibration generator for transmitting vibrations to the atomizing element, and a switch disposed in the displacement path of the slideable member, the switch being activatable by the displacement of the slideable member for operating the atomizing element and vibration generator.

In accordance with yet an added feature of the invention, the switch is operable to activate the transporting means subsequent to operating the vibration generator, which is preferably an ultrasonic-flexural vibration generator.

In accordance with yet an additional feature of the invention, the housing includes a main housing body containing the slide, housing support, atomizing element and vibration generator, a cover part having a spout formed therein for the discharge of fluid, and a further housing part into which batteries are insertable.

In accordance with a concomitant feature of the invention, there is provided a removable cap covering the spout.

As already mentioned the atomizer for fluids according to the invention is particularly useful for medical applications, especially for asthma patients. But it can also be advantageously used as a room or body spraying device, wherein the metering of the fluid is not required.

Other features which are considered as characteristic for the invention are set forth in the appended claims.

Although the invention is illustrated and described herein as embodied in an atomizer for fluids, preferably an inhalation device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic perspective view of the entire atomizer for fluids according to the invention;

FIG. 4 is an exploded view of the atomizer for fluids according to FIGS. 1 to 3.

Figure 2:
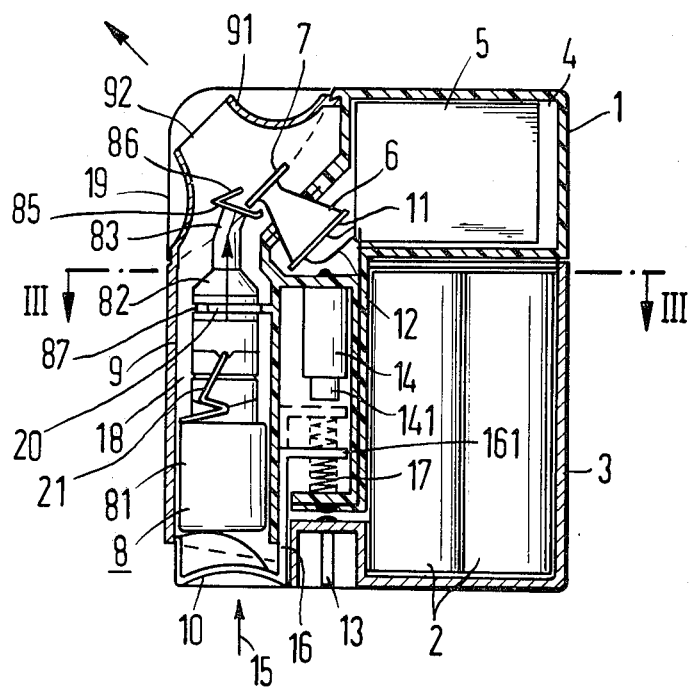
FIG. 2 is a longitudinal sectional view of the atomizer for fluids according to FIG. 1.
Figure 3:
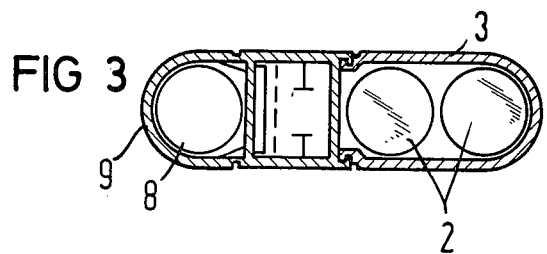
FIG. 3 is a top plan view along the section line III—III in FIG. 2, in the direction of the arrows.

Referring now to all of the figures of the drawing as a whole, there is seen an illustration of the atomizer for fluids according to the invention which is shown as a pocket inhalation device. The device comprises the following parts: an L-shaped main-housing body 1, a housing part 3 containing a set of batteries 2, the housing part 3 being insertable in the main housing body 1, an electronic vibration generator 5 disposed in an upper chamber 4 of the main housing body 1, connected to an atomizing element 6 with an atomizer plate 7, a fluid dispenser 8, a cover 9 which can be pushed onto the main housing body 1, and also an operating member or organ 10 which can be manually operated. The atomizing element 6 includes a cone-shaped vibrator or sound transducer which is provided on one side thereof with a piezo-ceramic layer 11 and which supports the atomizer plate 7 on the other side thereof. The atomizer element 6 is electrically connected to the electronic vibration generator 5 through the electrical leads 12. Ultrasonic vibrations are transmitted through the leads 12 from the generator 5 to the atomizer element 6. In order to operate the vibration generator 5, there are provided the batteries 2 and a built-in accumulator which can be plugged into a charging device by means of a contact 13. The charging device is connected to the current network for re-charging the accumulator. When the fluid from the dispenser 8 reaches the atomizer plate 7 which is activated or excited by the vibration generator 5, the fluid is atomized into a fine mist, and thrown out in the direction of the arrow through an atomizing funnel or spout 91 having an atomizing orifice 92. The vibration generator 5 is turned on by a push-button switch 14 having a switch element 141. Part of the main housing body 1 is a slideable member or slide 16, which again is a part of the slightly curved inner pressure surface of the operating member 10.

As shown in FIG. 2, the slide 16 can be slid in the direction of the arrow 15 along a guide surface, shown vertically oriented in FIG. 2, against the force of a spring 17, upward in FIG. 2 into the position shown in dotted lines. An angled projection 161 of the slide 16 therefore serves for supporting the spring 17, and also for operating the switch 14. In the region of the operating member 10, the slide 16 forms a storage space 18 for the fluid dispenser 8 together with the surrounding walls of the main housing body; this storage space 18 can be closed by the hereinbefore mentioned cover 9 after the fluid dispenser 8 has been put in place. The atomizer funnel or spout 91 with the atomizer opening 92 is made in a one-piece unitary assembly with the cover 9. A closure cap 19 can be push-fitted onto the atomizer funnel 91.

As shown particularly in FIGS. 2 and 4, the fluid dispenser 8 is in the form of a cylindrical, cartridge-like fluid container, basically comprising two parts: a lower part 81 which contains the fluid supply, and an upper part 82. The lower part 81 is slideable with respect to the upper part 82 against the force of a spring. The upper part 82 is provided with a cylindrical portion 83 of lesser diameter which is perforated by a discharge channel with a discharge orifice 84. At the free end of the cylindrical portion 83, within the region of the discharge orifice 84, there is a preparatory organ in the form of an open pan 85 which is open toward the atomizing element 6. In this way the concave pan 85 is provided with a V-angled rebound shield 86 which extends over the discharge orifice 84. In the interior of the fluid dispenser 8, there are provided non-illustrated conventional displacement-transport means in form of a fluid pump, for example, which is operated by compressing the two cylindrical parts 81 and 82, and including a one way valve as well. Furthermore the space in the fluid container which is not filled with liquid, can be filled with a gas, which always effects a positive pressure in the fluid dispenser. In the upper part 82 of the fluid dispenser 8 there is provided an annular tee-slot 87 which is retainable as part of the main housing body 1 by means of a pan-like and rib-shaped housing-support 20, when the fluid dispenser is inserted into the storage space 18. Thus a fixed relationship is established between the upper part 82 of the fluid dispenser 8, and the atomizing element 6 and the atomizer plate 7, so that the atomizer plate 7 dips with its edge into the pan 85, as shown in FIG. 2. To arrest the upper part 82 of the fluid dispenser 8 a spring element 21 which is supported at the main housing body 1, can also be provided. The spring element 21 can be used by itself or as an additional element.

For operating the fluid atomizer, the closure cap 19 is removed and the person operating the device, an asthma sufferer for example, presses his thumb on the operating member 10 of the slide 16. The slide 16 in FIG. 2 therefore moves upwardly, so that the position of the switch 14 is such that first the switch 14, and through it the vibration generator 5 and the atomizing element 6, are activated. Then, after further motion of the slide 16, the means for displacing and transporting, i.e. the discharge valve and the displacement transport device in the dispenser 8 are operated, by relatively displacing the lower part 81 with respect to the upper part 82 of the fluid dispenser 8 to squeeze the two parts together and eject a certain amount of fluid. Thereby an exactly metered amount of fluid, corresponding to the performed stroke, flows into the pan 85, whereby the rebound shield 86 reflects the discharged jet of fluid in the direction of the pan. The transported liquid now comes in contact with the atomizer plate 7 which is, for example, covered with a fabric-like cover. As explained hereinbefore, the liquid is then expelled through the atomizer opening 92, in the form of a fluid mist, to the exterior and into the breathing passages of the asthma sufferer.

Obviously, the possibility exists within the scope of the invention, to direct the fluid jet, which is discharged from the fluid dispenser, directly onto the atomizer plate 7, if the discharge orifice 84 of the fluid dispenser is turned toward the surface of the atomizer plate 7.

There are claimed:

1. Atomizer for fluid, comprising an atomizer housing, a unitary fluid container removably inserted in said housing, an atomizing element activatable by ultrasonic flexural vibrations being disposed in said housing, manually operable means integral with said fluid container for transporting the fluid from said fluid container to said atomizing element, and manually activatable means for operating said transporting means and atomizing element.

2. Atomizer according to claim 1, wherein said fluid container is air tight and includes means for readying a metered portion of fluid for transport, and said transporting means is operable to transport said metered portion of fluid.

3. Atomizer according to claim 2, including a discharge orifice formed in said housing, and a preparatory element in vicinity of said orifice and atomizing element for retaining said metered portion of transported fluid.

4. Atomizer according to claim 3, wherein said preparatory element is a pan having an opening formed therein facing said atomizing element, and including a fluid rebound shield integral with said pan and extending over said orifice.

5. Atomizer according to claim 1, wherein said fluid container has two parts which are compressible for activating said transporting means and including a slideable member disposed in said housing, a housing support for fixing one of said parts in position relative to said atomizing element, and a spring exerting a force on said member in a given direction, said fluid container being insertable in said slideable member and said slideable member being manually displaceable in said housing against said given direction for compressing said parts.

6. Atomizer according to claim 5, including a vibration generator for transmitting vibrations to said atomizing element, and a switch disposed in the displacement path of said slideable member, said switch being activatable by said displacement of said slideable member for operating said atomizing element and vibration generator.

7. Atomizer according to claim 6, wherein said switch is operable to activate said transporting means subsequent to operating said vibration generator.

8. Atomizer according to claim 5, wherein said housing includes a main housing body containing said slideable member, housing support, atomizing element and vibration generator, a cover part having a spout formed therein for the discharge of fluid, and a further housing part into which batteries are insertable.

9. Atomizer according to claim 8, including a removable cap covering said spout.

* * * * *